United States Patent [19]

Immel et al.

[11] Patent Number: 5,304,525

[45] Date of Patent: Apr. 19, 1994

[54] CATALYST FOR THE PREPARATION OF ANILINE

[75] Inventors: Otto Immel, Krefeld; Helmut Waldmann, Leverkusen; Rudolf Braden, Odenthal-Scheuren; Christian Fröhlich, Krefeld; Gerhard Friedhofen, Krefeld; Wilfried Niemeier, Krefeld, all of Fed. Rep. of Germany

[73] Assignee: Bayer Aktiengesellschaft, Leverkusen, Fed. Rep. of Germany

[21] Appl. No.: 50,752

[22] Filed: Apr. 21, 1993

Related U.S. Application Data

[63] Continuation of Ser. No. 797,875, Nov. 26, 1991, abandoned.

[30] Foreign Application Priority Data

Dec. 7, 1990 [DE] Fed. Rep. of Germany ....... 4039026

[51] Int. Cl.$^5$ .............. B01J 21/18; B01J 23/40
[52] U.S. Cl. .................. 502/185; 502/180; 502/326; 564/423
[58] Field of Search ........ 502/185, 180, 326; 564/423

[56] References Cited

U.S. PATENT DOCUMENTS

| | | | |
|---|---|---|---|
| 3,458,576 | 7/1969 | Bryan | 502/326 |
| 3,719,739 | 3/1973 | Thompson | 502/326 |
| 3,882,048 | 5/1975 | Thelen et al. | 502/174 |
| 4,265,834 | 5/1981 | Birkenstock et al. | 564/421 |
| 4,407,733 | 10/1983 | Birkenstock et al. | 502/174 |
| 4,415,479 | 11/1983 | Puskas et al. | 502/185 |
| 4,467,110 | 8/1984 | Puskas et al. | 502/185 |
| 4,777,303 | 10/1988 | Kitson et al. | 502/185 |
| 5,061,671 | 10/1991 | Kitson et al. | 502/185 |

FOREIGN PATENT DOCUMENTS 0011090 5/1980 European Pat. Off. .

OTHER PUBLICATIONS

*Chemical Abstracts* (25—Noncondensed Aromatics), vol. 78, 1973, p. 453; 124248s, Ger. Offen. 2,135,155.
Journal of Chemical Society, Chemical Communications, 1981, pp. 540–541.

*Primary Examiner*—Asok Pal
*Attorney, Agent, or Firm*—Sprung Horn Kramer & Woods

[57] ABSTRACT

A process for the preparation of aniline by hydrogenation of nitrobenzene in the gas phase in the presence of a catalyst containing a noble metal is described. The process can be carried out in an improved manner if the catalyst employed is palladium on graphite or petrol coke, as the support, containing 0.001–1% by weight of Pd, based on the total weight of the catalyst, it being possible for the catalyst also to contain, in addition to the Pd, 0.001–0.5% by weight of Ir and/or 0.001–0.3% by weight of Rh, all figures being based on the total weight of the catalyst.

7 Claims, No Drawings

CATALYST FOR THE PREPARATION OF ANILINE

This application is a continuation of application Ser. No. 797,875, filed Nov. 26, 1991, now abandoned.

BACKGROUND OF THE INVENTION

1. Field of the Invention

The present invention relates to an improved process for the preparation of aniline by catalytic hydrogenation of nitrobenzene in the gas phase.

Aniline is known to the expert as an important intermediate product, for example for the preparation of dyestuffs and polyurethanes.

2. Description of the Related Art

Palladium-containing supported catalysts are known for the hydrogenation of nitrobenzene and other nitroaromatics. In addition to the catalytically active metal, the materials employed as the catalyst support are also decisive for the activity of a catalyst. Because of their surface nature, these support materials can lead to the formation of undesirable by-products. Aluminium oxides which have been converted completely or partly into spinel are known as supports from DE-OS (German Published Specification) 2,135,155 and DE-OS (German Published Specification) 2,244,401. Further processes for the hydrogenation of nitrobenzene are known from DE-OS (German Published Specification) 2,848,978 and DE-OS (German Published Specification) 2,849,002.

The catalysts known to date for the hydrogenation of nitroaromatics in the gas phase show disadvantages which limit their use in the chemical industry. Thus, although the initial yield in the hydrogenation of nitrobenzene to aniline is quite high at 99%, the known catalysts rapidly lose their activity, for example by poisoning or by the deposition of tar-like precipitates, so that only short service lives result. In this case,, the hydrogenation must be interrupted in order to regenerate the catalyst. The frequent interruptions and the expensive nature of the regeneration are uneconomical for large-scale industrial plants. A further disadvantage of the catalysts known to date is their irregular activity, which frequently manifests itself in an over-reactivity to give undesirable by-products. If larger concentrations of noble metal or diverse combinations of different elements are used to increase the service life, the high noble metal requirement has the effect of an undesirable cost-causing agent in the industrial realisation of such processes (DE-OS (German Published Specification) 2,849,002). Such catalysts prepared from many elements are moreover more cumbersome to prepare and to dispose of.

SUMMARY OF THE INVENTION

It has been found that the preparation of aniline by catalytic hydrogenation of nitrobenzene in the gas phase can be carried out with a considerably improved catalyst loading coupled with unexpectedly long service lives if the hydrogenation is carried out in the presence of a supported catalyst which contains Pd or a combination of Pd with Ir and/or Rh and/or Ru on graphite or graphite-containing coke.

The invention accordingly relates to a process for the preparation of aniline by hydrogenation of nitrobenzene in the gas phase in the presence of a catalyst containing a noble metal, which is characterised in that the catalyst employed is palladium on graphite or graphite-containing coke, as the support, containing 0.001–1.5% by weight of Pd, based on the total weight of the catalyst, it being possible for 0–40 per cent of the Pd, relative to its amount, to be replaced by Ir and/or Rh and/or Ru.

The invention furthermore relates to a catalyst which contains 0.001–1.5% by weight of Pd, based on the total weight of the catalyst, on graphite or graphite-containing coke, as the support, it being possible for 0–40 per cent of the Pd, relative to its amount, to be replaced by Ir and/or Rh and/or Ru.

DETAILED DESCRIPTION OF THE INVENTION

The catalysts according to the invention thus contain the noble metal(s) in the following arrangements on the support: Pd by itself, Pd/Ir, Pd/Rh, Pd/Ru, Pd/Ir/Rh, Pd/Ir/Ru, Pd/Rh/Ru or Pd/Ir/Rh/Ru. In many cases, one of the two-component combinations mentioned or Pd by itself is employed.

The palladium is preferably present in the catalysts according to the invention in an amount of 0.005–1% by weight, preferably 0.05–0.5% by weight, based on the total weight of the catalyst. The lower limit zero of the percentages of the other platinum metals mentioned, relative to their amount, indicates the use of Pd by itself. If the other platinum metals are employed, their content is preferably 10–40 per cent in total, relative to the total amount of platinum metals; amongst themselves, their weight ratio is 1:1–3:1 between each two.

It has furthermore proved to be advantageous for the catalysts mentioned additionally to be doped with a sulphur-containing or phosphorus-containing, preferably phosphorus-containing, compound. Such an additional content of doping agent is 0.1–2% by weight, preferably 0.1–1% by weight, of sulphur or phosphorus, preferably phosphorus, in chemically bound form, based on the total weight of the catalyst. Preferred phosphorus-containing compounds which may be mentioned for doping the catalysts according to the invention are: the oxygen acids of phosphorus $H_3PO_4$, $H_3PO_3$ or $H_3PO_2$, or alkali metal salts thereof, such as, for example, sodium dihydrogen phosphate, sodium or potassium phosphate or sodium hypophosphite.

The catalysts according to the invention are characterised by their support made of a graphite-containing material. Such materials are the graphites themselves and cokes, such as needle coke or petrol coke. These supports have a BET surface area of 0.2–10 $m^2/g$.

To prepare the catalysts according to the invention, a procedure can be followed in which the noble metals mentioned, in the form of suitable salts, and the sulphur-containing or phosphorus-containing compound are applied in separate working operations to one of the supports mentioned in the form of pellets, beads, extruded granules or fragments about 1–10 mm in dimension, the support being dried after each application. Drying is carried out in a known manner, for example at 100°–140° C. and under reduced to normal pressure, for example under 1–1,000 mbar; a possible reduced pressure is, for example, that of a water-pump. Aqueous solutions can be used for impregnating the support. This is preferably the case with the sulphur- or phosphorus-containing compounds, of which the water-soluble compounds are preferred. However, the noble metal salts are preferably dissolved and applied in organic solvents, such as simple alcohols, ketones, cyclic ethers or nitriles. Examples of such organic solvents are methanol, ethanol, propanol, isopropanol, acetone, methyl ethyl ketone, dioxane, acetonitrile and comparable solvents. In the case of salts with organic anions, methylene chloride and comparable solvents can also be employed. Examples of suitable salts of the noble metals are their chlorides, nitrates or acetates.

The catalyst according to the invention is available after the impregnation and the subsequent drying. It is preferably activated in the reactor before the start of the hydrogenation of nitrobenzene by treatment with hydrogen at elevated temperature. Such an elevated temperature is, for example, in the range of 200°–450° C., preferably in the range of 220°–420° C.

The catalysts mentioned can be used in an outstanding manner for the hydrogenation of nitrobenzene to give aniline. Such a hydrogenation is carried out in the gas phase in a wide pressure range, which extends from reduced pressure via normal pressure and only moderately increased pressure up to a high pressure, and can be expressed numerically by the range of 0.5–100 bar. While the reaction can thus certainly be carried out under a high pressure, for example 10–100 bar, the variant under reduced pressure, normal pressure or only moderately increased pressure is preferred. The use of normal pressure is particularly preferred, because of simplification of the apparatus. A temperature of 250°–450° C., preferably 350° to 420° C., is established for the hydrogenation. To establish this temperature, a contribution is made by external heating around the reactor or the reactor tubes, for example by a circulating heat transfer medium or adjacent electrical hotplates; the supplementary contribution is the exothermic heat of hydrogenation, which varies in content according to the temperature level, the substrate and in particular the residence time and the dilution with $H_2$.

A catalyst loading of 0.1–2 kg, preferably 0.2–0.9 kg, of nitrobenzene per liter of catalyst and hour is established for the process according to the invention.

A nitrobenzene of the formula

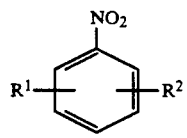

(I)

wherein $R^1$ and $R^2$ independently of one another represent hydrogen, methyl, ethyl, propyl or butyl, preferably methyl or ethyl, is employed according to the invention.

The hydrogenating hydrogen is employed in an amount of 1–100 standard liters per 1 g of nitrobenzene employed, preferably 1–50 standard liters.

If the activity of the catalyst according to the invention decreases, the catalyst can easily be regenerated in situ, that is to say in the hydrogenation reactor. For this, the catalyst is treated at 350°–440° C. successively with steam, a nitrogen/air mixture or atmospheric air and finally nitrogen. The treatment with steam can be carried out for 1 to 3 hours and the treatment with air or the nitrogen/air mixture can be carried out for 1 to 4 hours. Treatment with hydrogen at 200°–350° C. follows for renewed activation of the catalyst. Such a regeneration is not possible with noble metal catalysts on activated carbon as the support, since an activated carbon starts to burn during such a regeneration.

EXAMPLE 1

400 g of petrol coke granules of particle size 2 to 8 mm and with a BET surface area of 4.3 $m^2/g$ were impregnated with a solution of 1.668 g of Pd acetate in 72 g of acetonitrile and then dried at 100° C.

50 g of the petrol coke impregnated in this way with 0.2% by weight of Pd were additionally impregnated with a solution which had been prepared from 0.029 g of $IrCl_4.H_2O$ and 9 g of methanol. The impregnated granules were dried at 100° C. for 18 hours. They contained 0.03% by weight of iridium.

After drying, 15 ml (10.1 g) of the catalyst thus prepared were introduced into a reaction tube which had an internal diameter of 17 mm and a length of 60 cm. The reaction tube was inserted into a double-walled steel tube, which was arranged vertically and was kept at 300° C. with an oil thermostat. In order to activate the catalyst, only hydrogen (30 l/h) was initially passed over the catalyst at 300° C. for 4 hours.

Nitrobenzene was then also admixed to the stream of hydrogen (30 l/hour) at a metered rate, and the temperature of the oil thermostat was kept at 300° C. The reaction product had the following composition, depending on the operating time (hours) of the catalyst (the remainder to make up 100% comprises by-products).

| Time hours | Loading g/ml.hour | Nitrobenzene % | Aniline % |
| --- | --- | --- | --- |
| 303 | 0.65 | 0.1 | 99.6 |
| 821 | 0.78 | 0.1 | 99.1 |
| 1485 | 0.67 | 0.6 | 99.1 |
| 1856 | 0.65 | 0.1 | 99.6 |
| 2733 | 0.64 | 0.2 | 99.4 |

The water of reaction was not taken into account in the composition of the reaction product.

EXAMPLE 2

5.2 ml (14.2 g) of graphite granules which had been impregnated with 0.025% of Pd and 0.05% of Rh were used as the catalyst for the hydrogenation of nitrobenzene. After 4195 operating hours of the catalyst, the hydrogenation produced a reaction product which contained 98.2% of aniline and 1.6% of nitrobenzene. The catalyst loading in this reaction was 0.5 g of nitrobenzene/ml.hour, and the temperature in the reaction furnace was 300° C. In order to regenerate the catalyst, the hydrogenation was interrupted and the reaction tube was heated to 420° C. 20 l of air/hour and 5 g of water/hour were then passed over the catalyst layer for 5 hours. Thereafter, the catalyst was first activated with hydrogen (30 l/hour) at 300° C. for 1 hour, before the hydrogenation of nitrobenzene was continued. The hydrogenation then produced a reaction product containing 99.4% of aniline, 0.4% of nitrobenzene and 0.2% of by-products. The water of reaction was not taken into account in the analysis.

EXAMPLE 3

100 g of petrol coke granules of particle size 2 to 8 mm and with a BET surface area of 4.3 $m^2/g$ and a bulk density of 630 g/l were impregnated with a solution of 0.471 g/l of Pd acetate in 18 ml of acetonitrile and then dried at 100° C. 15 ml of the catalyst prepared in this way were employed for the hydrogenation of nitrobenzene as in Example 1. The catalyst, which contained 0.1% by weight of Pd, was first reduced with hydrogen at 280° C. for 3.5 hours. Nitrobenzene was then also mixed with the stream of hydrogen at a metered rate and reacted over the catalyst. 68,653 g of nitrobenzene were passed through the catalyst layer in the course of 5737 hours. This corresponds to a catalyst loading of 0.8 g/ml.hour. At a heating temperature of 300° C., the reaction product contained 98.9% of aniline and 0.9% of nitrobenzene after 3891 hours and 98.0% of aniline and 1.7% of nitrobenzene after 5737 hours (the remainder to make up 100% are byproducts). The water of reaction was not taken into account in the composition.

EXAMPLE 4

100 g of graphite granules of particle size 2–6 mm and with a BET surface area of 0.9 m$^2$/g were impregnated with a solution which was prepared from 0.104 g of Pd(CH$_3$COO)$_2$ and 6 g of acetonitrile. The impregnated graphite granules were dried at 100° C. for 18 hours. 15 ml (14.4 g) of the catalyst prepared in this way were used for the hydrogenation of nitrobenzene as in Example 1. The amount of Pd with which the catalyst had been impregnated corresponded to 0.05% of Pd, based on the total weight of the catalyst. In order to activate the catalyst, 30 l of hydrogen per hour were first passed over the catalyst at 280° C. for 4 hours. The hydrogenation of nitrobenzene was then started, the heating temperature in the reaction furnace still being kept at 280° C.

A total of 49,906 g of nitrobenzene were passed over the catalyst in the course of 5782 hours. This corresponds to an average catalyst loading of 0.58 g/ml.hour. After 3717 hours, the reaction product contained 99.6% of aniline and 0.1% of nitrobenzene; after the experiment had been carried out for 5772 hours, 99.5% of aniline and 0.1% of nitrobenzene were found in the reaction product. The content of by-products was 0.3–0.4%.

EXAMPLE 5

50 g of a commercially available electrographite of particle size 2–6 mm were impregnated with a solution which had been prepared from 0.1045 g of PD(CH$_3$COO)$_2$ and 2.3 g of dioxane. The impregnated graphite granules were dried at 100° C. for 18 hours. 30 g of the graphite granules treated in this way were impregnated again with a solution which had been prepared from 0.1027 g of NaH$_2$PO$_2$.H$_2$O and 1.3 g of methanol. After drying again, 10 ml (10 g) were used for the hydrogenation of nitrobenzene. The amount of Pd with which the catalyst had been impregnated corresponded to 0.1% by weight of Pd, and the amount of sodium hypophosphite solution with which the catalyst had been impregnated corresponded to 0.1% by weight of P, based on the total weight of the catalyst. In order to activate the catalyst, 30 l of hydrogen per hour were first passed over the catalyst at 280° C. for 4 hours. The hydrogenation of nitrobenzene was then carried out, the heating temperature in the reaction furnace still being kept at 280° C. The catalyst loading was 0.63 to 0.82 g of nitrobenzene/ml of catalyst × hour. After 1958 operating hours of the catalyst, still no loss in activity could be found.

The reaction product had the following composition, depending on the duration of use of the catalyst (the remainder to make up 100% comprises by-products):

| Time (hours) | Loading g/ml.hour | Nitrobenzene (%) | Aniline % |
| --- | --- | --- | --- |
| 91 | 0.80 | 0.1 | 99.4 |
| 854 | 0.78 | 0.3 | 99.4 |
| 1361 | 0.81 | 0.4 | 99.4 |
| 1450 | 0.75 | 0.4 | 99.4 |
| 1958 | 0.74 | 0.3 | 99.4 |

EXAMPLE 6

300 g of a commercially available needle coke of particle size 1.5–4 mm and with a BET surface area of 0.8–1 m$^2$/g were impregnated with a solution which had been prepared from 0.625 g of Pd acetate and 105 g of methylene chloride. After intermediate drying at 100° C., 100 g of the needle coke impregnated with Pd were impregnated again with a solution which had been prepared from 0.068 g of NaH$_2$PO$_4$.H$_2$O and 35 g of methanol. The impregnated needle coke was then dried at 100° C. for 18 hours.

10 ml (8.5 g) of the catalyst prepared, which contained 0.1% by weight of Pd, were introduced into a reaction tube which had an internal diameter of 17 mm and a length of 70 cm. It was heated to 280° C. in a vertically arranged electrical furnace. In order to activate the catalyst, only hydrogen (30 l/hour) was passed through the catalyst for 1 hour. Hydrogen (30 l/hour) and nitrobenzene in a metered amount were then reacted at a heating temperature of 280°C. The reaction product was condensed and analysed by gas chromatography. The reaction product had the following composition, depending on the operating time of the catalyst (the remainder to make up 100% are byproducts):

| Time (hours) | Catalyst loading g/ml.hour | Nitrobenzene (%) | Aniline % |
| --- | --- | --- | --- |
| 117 | 0.75 | 0.1 | 99.2 |
| 487 | 0.82 | 0.1 | 99.3 |
| 726 | 0.96 | 0.1 | 99.5 |
| 919 | 0.69 | 0.1 | 99.5 |
| 1264 | 0.76 | 0.1 | 99.5 |

EXAMPLE 7 (for comparison)

100 g of commercially available active charcoal granules in the form of 4 mm extruded granules (from Carbo-Tech, type C 40/4) with a BET surface area of 1,200±50 m$^2$/g, were impregnated with a solution which had been prepared from 2.09 g of Pd acetate and 75 g of acetonitrile. The active charcoal granules impregnated with Pd were dried at 100° C. for 18 hours. The amount of Pd with which the catalyst had been impregnated corresponded to 1% by weight of Pd, based on the active charcoal employed. 10 ml (4.3 g) of the catalyst prepared in this way were introduced into a glass tube 17 mm wide and were first activated in a stream of hydrogen (30 l/hour) at 280° C. for 1 hour. During this procedure, the glass tube was in a vertically arranged electrical furnace. Nitrobenzene was then passed over the catalyst at a rate of 0.71 g/ml catalyst × hour, the stream of hydrogen being 30 l/hour and the heating temperature in the reaction furnace being kept at 280° C. The reaction product formed in the course of 162 hours contained
  96.2% of aniline
  0.4% of nitrobenzene 3.4% of by-products The water of reaction was not taken into account in the analysis.

EXAMPLE 8

Graphite granules (2-8 mm) with a BET surface area of 0.9 m$^2$/g and active charcoal granules (4 mm extruded granules) with a BET surface area of 1200±50 m$^2$/g were impregnated in the same manner with in each case 0.1% by weight of Pd. In each case 10 g of the two types of granules were heat-treated in an open crucible, with access of air, at 420° C. for in each case 3 hours. The following weight losses were then determined:

graphite (0.1% of Pd): 0.22%
active charcoal (0.1% of Pd): 10.1%

In the case of deactivation of a Pd-graphite or a Pd-active charcoal catalyst, such heat treatment at 380°-450° C. is necessary in order to achieve regeneration. The comparison experiment shows that the heat treatment for regeneration of the Pd/activated carbon catalyst is associated with losses which are too high.

What is claimed is:

1. A catalyst comprising a graphite or graphite-containing coke having a BET surface area of 0.2-10 m$^2$/g, as a support, impregnated with from 0.001 to 1.5% by weight of Pd, said catalyst having been prepared by impregnating said support with said Pd in the form of a salt which salt is reduced to elemental Pd upon activation of the catalyst.

2. The catalyst of claim 1, having a content of Pd in an amount of 0.005-1% by weight.

3. The catalyst of claim 2, having a content of Pd in an amount of 0.05-0.5% by weight.

4. The catalyst of claim 1, having an additional content of 0.1-2% by weight of a sulphur-containing or phosphorus-containing compound, calculated as sulphur or phosphorus, based on the total weight of the catalyst.

5. The catalyst of claim 4, having an additional content of 0.1-1% by weight of sulphur-containing or phosphorus-containing compound, calculated as sulphur or phosphorus, based on the total weight of the catalyst.

6. A catalyst comprising graphite or graphite-containing coke having a BET surface area of 0.2-10 m$^2$/g, as a support, and Pd and a metal selected from the group consisting of Ir, Rh, Ru and mixtures thereof wherein the total amount of Pd and said metal selected from the group consisting of Ir, Rh, Ru and mixtures thereof is from 0.001-1.5% by weight of the total weight of the catalyst, and the amount of said metal selected from the group consisting of Ir, Rh, Ru and mixtures thereof is up to 40% by weight of the total weight of Pd and said metal, and wherein said catalyst is prepared by impregnating said support with said Pd and said metal in the form of salts, which salts are reduced to elemental Pd and the elemental form of said metal upon activation of the catalyst.

7. The catalyst of claim 6, wherein the total amount of Pd and said metal selected from the group consisting of Ir, Rh, Ru and mixtures thereof is from 0.005-1% by weight, and the total amount of said metal selected from the group consisting of Ir, Rh, Ru and mixtures thereof is 10-40% by weight of the total amount of Pd and said metal.

* * * * *